United States Patent
Ponomarev et al.

(10) Patent No.: US 9,970,913 B2
(45) Date of Patent: May 15, 2018

(54) MULTI-COMPONENT SENSING COATING FOR PRESSURE AND TEMPERATURE MEASUREMENTS

(71) Applicant: THE BOEING COMPANY, Chicago, IL (US)

(72) Inventors: Sergey G. Ponomarev, Seattle, WA (US); James Douglas McLean, Seattle, WA (US)

(73) Assignee: THE BOEING COMPANY, Chicago, IL (US)

(*) Notice: Subject to any disclaimer, the term of this patent is extended or adjusted under 35 U.S.C. 154(b) by 572 days.

(21) Appl. No.: 14/502,922

(22) Filed: Sep. 30, 2014

(65) Prior Publication Data

US 2016/0091475 A1    Mar. 31, 2016

(51) Int. Cl.
| | |
|---|---|
| *C09D 5/22* | (2006.01) |
| *G01N 33/00* | (2006.01) |
| *G01L 11/00* | (2006.01) |
| *G01M 9/02* | (2006.01) |
| *G01K 13/00* | (2006.01) |
| *B29C 67/00* | (2017.01) |
| *C09K 11/06* | (2006.01) |

(Continued)

(52) U.S. Cl.
CPC ..... *G01N 33/0036* (2013.01); *B29C 67/0059* (2013.01); *C09D 5/22* (2013.01); *C09K 11/06* (2013.01); *G01K 11/20* (2013.01); *G01K 13/00* (2013.01); *G01L 11/00* (2013.01); *G01L 11/02* (2013.01); *G01M 9/02* (2013.01); *G01M 9/06* (2013.01); *G01N 21/77* (2013.01); *B29K 2101/00* (2013.01); *B29K 2995/0035* (2013.01); *B29K 2995/0065* (2013.01); *B29K 2995/0067* (2013.01); *B29L 2009/005* (2013.01); *B33Y 10/00* (2014.12); *B33Y 80/00* (2014.12); *G01N 31/22* (2013.01); *G01N 2021/7786* (2013.01)

(58) Field of Classification Search
CPC ........... C09D 5/22; C09D 11/06; G01K 11/20
USPC ........................................................ 427/256
See application file for complete search history.

(56) References Cited

U.S. PATENT DOCUMENTS 5,341,676 A * 8/1994 Gouterman ............. G01M 9/06
                                                              250/459.1
5,359,887 A    11/1994 Schwab et al.
(Continued)

FOREIGN PATENT DOCUMENTS

EP    1715317 A1    10/2006
EP    1715319 A2    10/2006
(Continued)

OTHER PUBLICATIONS

Kameya et al. Dual luminescent arrays sensor fabricated by inkjet-printing of pressure-and temperature-sensitive paints. Sensors and Actuators B: Chemical. vol. 190 Jan. 2014.pp. 70-77.*

(Continued)

*Primary Examiner* — Cachet I Sellman
(74) *Attorney, Agent, or Firm* — Patterson + Sheridan, LLP

(57) ABSTRACT

An environment sensitive coating system is disclosed that includes a pressure sensitive component comprising a first portion of an oxygen sensitive light emitting material dispersed in an oxygen permeable binder; and a pressure reference component comprising a second portion of the oxygen sensitive light emitting material dispersed in an oxygen impermeable binder.

18 Claims, 3 Drawing Sheets

(51) Int. Cl.
| | |
|---|---|
| *G01L 11/02* | (2006.01) |
| *G01M 9/06* | (2006.01) |
| *G01K 11/20* | (2006.01) |
| *G01N 21/77* | (2006.01) |
| *B33Y 10/00* | (2015.01) |
| *B33Y 80/00* | (2015.01) |
| *B29K 101/00* | (2006.01) |
| *B29L 9/00* | (2006.01) |
| *G01N 31/22* | (2006.01) |

(56) References Cited

U.S. PATENT DOCUMENTS

| | | | |
|---|---|---|---|
| 6,607,300 B1 * | 8/2003 | Kleinerman | G01K 11/20 250/483.1 |
| 6,696,690 B2 | 2/2004 | Benne | |
| 7,176,272 B2 * | 2/2007 | Hamner | C08G 18/3215 528/73 |
| 7,290,444 B2 | 11/2007 | Kobayashi | |
| 7,513,685 B2 * | 4/2009 | Egami | C09D 5/22 252/408.1 |
| 7,690,842 B2 | 4/2010 | Bawendi et al. | |
| 2003/0111615 A1 | 6/2003 | Benne | |
| 2004/0249593 A1 | 12/2004 | Dunleavy et al. | |
| 2005/0288475 A1 | 12/2005 | Hamner | |
| 2006/0160241 A1 * | 7/2006 | Khalil | G01N 21/76 436/166 |
| 2007/0160500 A1 * | 7/2007 | Baumfalk | G01N 21/7703 422/82.07 |
| 2009/0272206 A1 * | 11/2009 | Stumpf | G01D 18/00 73/866.5 |
| 2010/0116017 A1 * | 5/2010 | Mayer | G01N 21/274 73/1.06 |

FOREIGN PATENT DOCUMENTS

| | | |
|---|---|---|
| EP | 2669340 A1 | 12/2013 |
| GB | 2283752 A | 5/1995 |

OTHER PUBLICATIONS

Hyakutake et al. Luminescent Multi-Layered Polymer Coating for the Simultaneous Detection of OxygenPressure and Temperature. Macromolecular Chemistry and Physics. 2009. 210,1230-1234.*
European Search Report for EP15183718, dated Mar. 1, 2016.

* cited by examiner

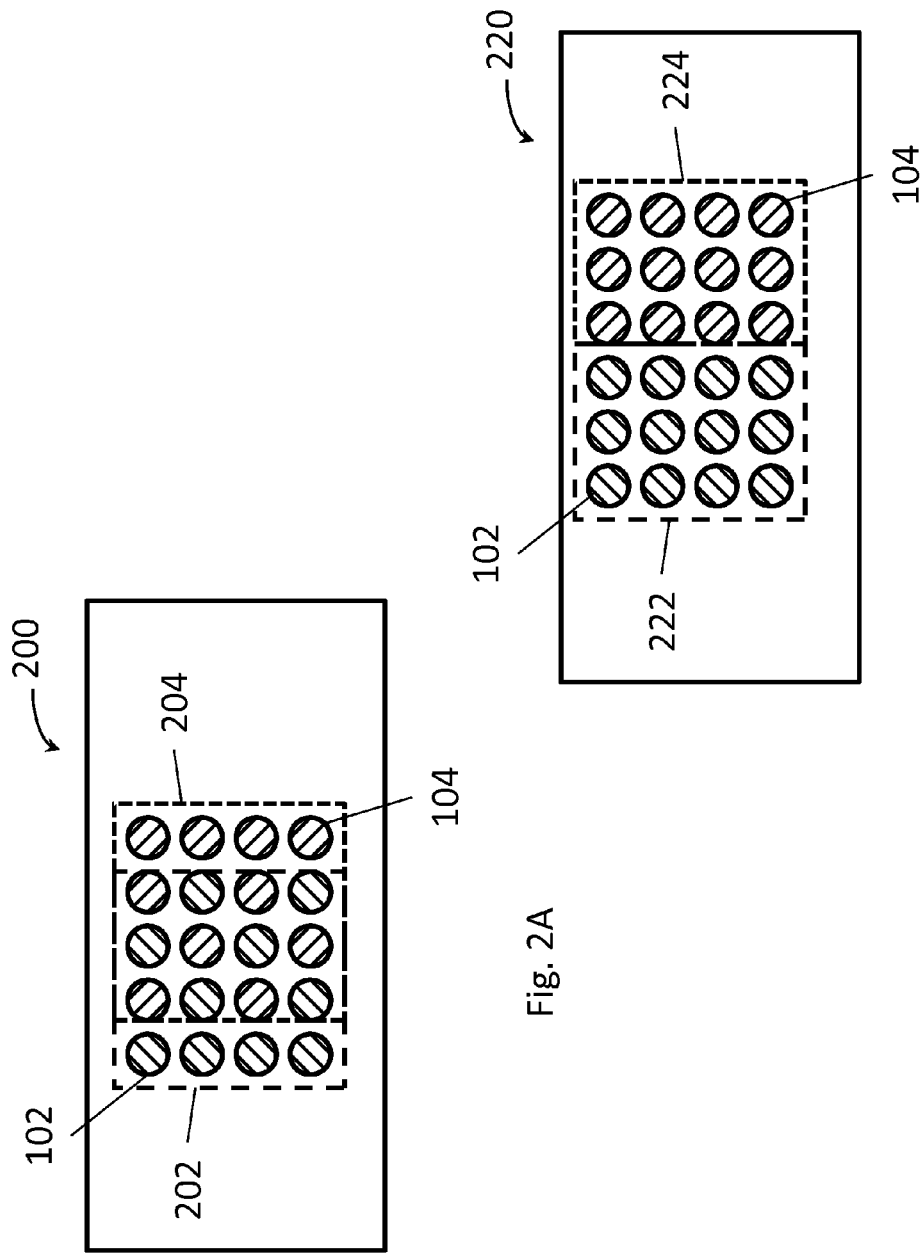

MULTI-COMPONENT SENSING COATING FOR PRESSURE AND TEMPERATURE MEASUREMENTS

FIELD

Embodiments described herein relate to light emitting pressure and temperature sensing coatings to measure air pressure, oxygen concentration, or temperature on solid surfaces and methods of applying such coatings.

BACKGROUND

Optical techniques have been used in the aerodynamics industry for many years to measure temperature and pressure on surfaces of wind tunnel models. Such techniques commonly employ coatings that emit light under ultraviolet or blue light illumination. The intensity of the emitted light is sensitive to pressure and temperature changes in and around the coating. The coatings are mainly of two types, pressure sensitive coatings and temperature sensitive coatings, and usually employ luminophors incorporated into some matrix, such as a polymeric binder. These coatings enable measurement of essentially continuous pressure and temperature field distributions along complex curved surfaces, limited only by the resolution of the imaging equipment used to capture variations in luminous intensity.

The coatings used in the past present certain challenges. First, non-uniform illumination of the surface and variation in coating thickness can give rise to variation in light emission by the coating that is not due to temperature or pressure variation. To remove such effects, a second luminophor that is not sensitive to pressure or temperature is commonly used as a reference. Additionally, sensitive luminophors typically have some sensitivity to both temperature and pressure that have to be decoupled to have an accurate representation of either. A pressure sensitive material is sometimes combined with a temperature sensitive material to provide compensation.

Combining two or more luminophors in a coating introduces other challenges. When multiple luminophors are illuminated by a single radiation field, the emitted light intensity of each luminophor is reduced. Also, one luminophor may emit light that is absorbed by another luminophor, complicating the measurement process. To compensate, the formulation of the coating with the two or more luminophors is typically balanced to provide optimum response, but the optimum may change with temperature and pressure conditions and age of the luminophors. In some cases, the two luminophors may be applied as two separate films, multiplying effects of thickness and concentration non-uniformity in the two films. Moreover, multi-wavelength systems typically have multiple cameras or detectors to register the different wavelengths, and the multiple detectors may have different characteristics that complicate obtaining accurate representations of temperature and pressure.

Coatings containing single luminophors also offer challenges. In systems with no reference luminophor, a first reference image is usually taken at a given temperature considered to be "cold", a second reference image is taken at a second temperature considered to be "hot", and the two reference images are normalized to each other. Such systems require frequent re-referencing as the luminophor ages. In some cases, the decay in luminous intensity between light-on and light-off conditions can be used to indicate temperature in a self-referenced procedure, but such procedures are often time-consuming and costly.

There is a need in the aerodynamics industry for improvement in the accuracy, effectiveness, and usability of pressure and temperature sensitive coatings.

SUMMARY

An environment sensitive coating system is disclosed that includes a pressure sensitive component comprising a first portion of an oxygen sensitive light emitting material embedded in an oxygen permeable binder; and a pressure reference component comprising a second portion of the oxygen sensitive light emitting material embedded in an oxygen impermeable binder.

Also disclosed is a method of applying an environment sensitive coating system to a substrate, comprising applying a pressure sensitive component comprising a first portion of an oxygen sensitive light emitting material embedded in an oxygen permeable binder in a first pattern to the substrate; and applying a pressure reference component comprising a second portion of the oxygen sensitive light emitting material embedded in an oxygen impermeable binder in a second pattern to the substrate.

Also disclosed is a method of applying an environment sensitive coating to a substrate comprising positioning the substrate on a work surface of a fluid patterning apparatus; flowing an environment sensitive coating precursor to a dispenser of the fluid patterning apparatus; applying energy to the environment sensitive coating precursor; dispensing the environment sensitive coating precursor onto the substrate in a plurality of dots having a predetermined pattern; and curing the environment sensitive coating precursor to form the environment sensitive coating.

Also disclosed is a method of measuring the pressure or oxygen concentration of an oxygen-containing fluid, comprising coating a substrate with an environment sensitive coating comprising a first portion with an oxygen sensitive light emitting material embedded in an oxygen permeable matrix and a second portion with the oxygen sensitive light emitting material embedded in an oxygen impermeable matrix; flowing an oxygen-containing fluid over the environment sensitive coating; irradiating the oxygen sensitive light emitting material with light having a wavelength that stimulates the oxygen sensitive light emitting material to emit light; measuring the intensities of light emitted by the oxygen sensitive light emitting material in the first portion and the second portion; and converting the measured intensities to a value of the fluid's pressure or oxygen concentration.

BRIEF DESCRIPTION OF ILLUSTRATIONS

FIG. 2A is a schematic view of a substrate having a first region populated with dots of a pressure sensitive component, and a second region, overlapping the first region, populated with dots of a pressure reference component, according to one embodiment.

FIG. 2B is a schematic view of a substrate having a first region populated with dots of a pressure sensitive component, and a second region, adjacent to the first region, populated with dots of a pressure reference component, according to another embodiment.

DETAILED DESCRIPTION

Figure 1B:
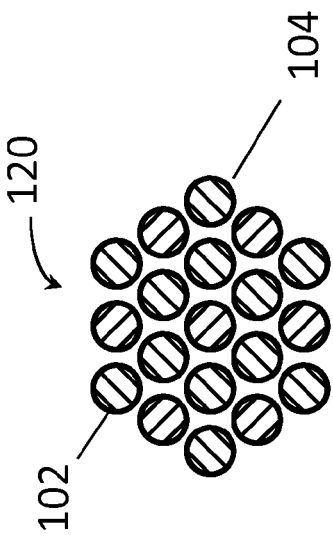
FIG. 1B shows a pattern of pressure detecting dots according to another embodiment.

The same light emitting material can be used as a pressure sensitive component and as a reference component, removing potential sources of error stemming from multiple cameras and illumination sources. A pressure sensitive component of an environment sensitive coating may comprise an oxygen sensitive light emitting material embedded in an oxygen permeable matrix. A pressure reference component of the same environment sensitive coating may comprise the same oxygen sensitive light emitting material embedded in an oxygen impermeable matrix. The light emitting material will exhibit a temperature response and a pressure response when embedded in the oxygen permeable matrix, and just a temperature response when embedded in the oxygen impermeable matrix. The temperature response may thus be separated from the pressure response to achieve a pressure measurement. Using the same light emitting material for both also provides reference for self-illumination by taking a single reading at wind-off conditions.

The light emitting material may be a compound or complex with a temperature-dependent response to oxygen. The light emitting material is generally fluorescent, and may be an aromatic material, such as a pyrene derivative, a quinoline derivative, erythrosines, phthalcyanines, aniline derivatives such as polyanilines, and porphyrin materials. Metal complexes of aromatic materials, such as platinum, osmium, iridium, rhodium, and ruthenium complexes, may be used. Platinum complexes such as tetra(pentafluorophenyl)porphine may be used as the light emitting material for both pressure sensitivity and temperature sensitivity. Other platinum porphyrin compounds that may be used include platinum tetra(pentafluorophenyl)porpholactone, platinum tetrabenztetraphenyl porphine, platinum tetrabenzporphine, platinum tetra(heptafluoropropyl)porphine, and platinum octaethylporphyrin.

For the pressure sensitive component, the light emitting material is embedded, dispersed, or dissolved in an oxygen permeable matrix, usually a polymer. Exemplary oxygen permeable materials that may be used as a host material for the pressure reference component include a random copolymer of heptafluoro-n-butyl methacrylate and hexafluoroisopropyl methacrylate, dimethylsiloxane-bisphenol A-polycarbonate block copolymer, poly(bisphenol A-carbonate) polymer, and polystyrene beads.

For the pressure reference component, the light emitting material is embedded, dispersed, or dissolved in an oxygen impermeable matrix. Oxygen impermeable materials that may be used have properties that allow the light emitting material to be exposed to thermal energy while minimizing exposure to oxygen. Thus, the oxygen impermeable matrix used for the pressure reference component will have some thermal permeability. Additionally, materials used for the pressure reference component have low absorptivity in radiation wavelengths absorbed and emitted by the light emitting material. Exemplary materials that may be used for the pressure reference component include chlorinated olefin polymers such as polyvinylidene chloride, and polyvinyl chloride (PVC), chlorinated PVC, chlorinated polyethylene, other chlorinated polyolefins, and physical or chemical mixtures thereof. Block and random copolymers and multipolymers of the foregoing may also be used. Poly(trifluorochloro)ethylene, poly(ethylene terephthalate) (PET), nylon, cellophane, polyvinyl alcohol, and ethylene vinyl alcohol may also be used.

A pressure sensitive component as described above may be made by multiple processes. In one embodiment, the light emitting material may be embedded or dissolved in a polymerizable monomer or mixture thereof to form a precursor mixture, which may then be polymerized by any suitable means. For example, the precursor mixture may be applied to a substrate prior to polymerization, and then heat, or other types of activating energy such as UV or visible radiation, may be applied to cure the mixture. Alternately, energy may be applied to the precursor mixture while the mixture is dispensed onto the substrate to start the curing process, and then the precursor mixture may be allowed to cure after being applied to the substrate. In another embodiment, the light emitting material may be embedded into a pre-formed polymer matrix by melting the polymer, mixing in the light emitting material, and then applying the mixture to the substrate. Such a process may be performed using an extruder or a mixer to melt the polymer. The precursor mixture may be applied to a substrate in the form of polymer dots using a fluid patterning apparatus such as a 3D printer or an inkjet printer. The precursor mixture may be hardened after application to the substrate by curing or drying.

In one aspect, a method of applying an environment sensitive coating to a substrate may be performed by positioning the substrate on a work surface of a 3D printer, flowing an environment sensitive coating precursor to a dispenser of the 3D printer, applying heat to the environment sensitive coating precursor, dispensing the environment sensitive coating precursor onto the substrate in a plurality of dots having a predetermined pattern, and curing the environment sensitive coating precursor to form the environment sensitive coating. The work surface may be movable in one, two, or three dimensions, and the 3D printer may be a gantry-type device, in which one or more print medium dispensers is coupled to a gantry of rails and carriages for positioning in three dimensions, or the 3D printer may be an articulated device having one or more articulated dispensers comprising a dispenser coupled to an articulated positioning arm.

The environment sensitive coating precursor may have one or more components. In one example the environment sensitive coating precursor has a pressure sensitive component and a pressure reference component. The pressure sensitive component may have a light emitting material, complex, or mixture, such as a platinum porphyrin compound, for example tetra(pentafluorophenyl) porphine, embedded in a reactive monomer or mixture thereof that produces an oxygen permeable polymer that is a reaction product of the reactive monomer or mixture, for example a mixture of heptafluoro-n-butyl methacrylate and hexafluoroisopropyl methacrylate. A solvent may be included to facilitate application and polymerization of the mixture. The pressure reference component may have the same light emitting material, complex, or mixture, embedded in a reactive monomer or mixture thereof that produces an oxygen impermeable polymer that is a reaction product of the reactive monomer or mixture, for example vinylidene chloride.

The precursors described above are flowed to a dispenser through separate paths, or through the same path at different times, for application to the substrate in different areas. The path or paths may be jacketed with a heat source to apply heat along any desired extent of the path. If heat is needed to start the polymerization reaction at the dispenser just before the precursor material is dispensed onto the substrate, a plenum may be provided around the exit path of the precursor from the dispenser to flow a heat transfer medium around, and in contact with, the exit point. Heat may thus be transferred into the precursor material as it exits the dispenser. Initiators may also be include in the precursor mixtures, if needed, to promote a polymerization reaction. For example, a peroxide initiator such as benzoyl peroxide may be included in the mixture with vinylidene chloride to initiate formation of poly(vinylidene chloride).

The pressure sensitive precursor and the pressure reference precursor may be dispensed onto the substrate using the 3D printer. The dispenser of the 3D printer is positioned according to a pattern, and a plurality of dots of each precursor are deposited on the substrate. The two precursors may be dispensed together, or all dots of the pressure sensitive precursor may be dispensed and then all dots of the pressure reference precursor may be dispensed.

In another aspect the pressure sensitive precursor and the pressure reference precursor may be dispensed onto the substrate using an inkjet printer. The precursors are provided to a dispenser of the inkjet printer, which is positioned with respect to the substrate to apply one or more jets of the precursor material to the substrate. The jet is formed by flowing the precursor through an opening in the dispenser at a velocity that results in substantially laminar flow for the geometry of the flow path. The viscosity of the precursor may be adjusted by any convenient means, for example by applying energy to the precursor or by adding a low viscosity solvent.

Figure 1A:
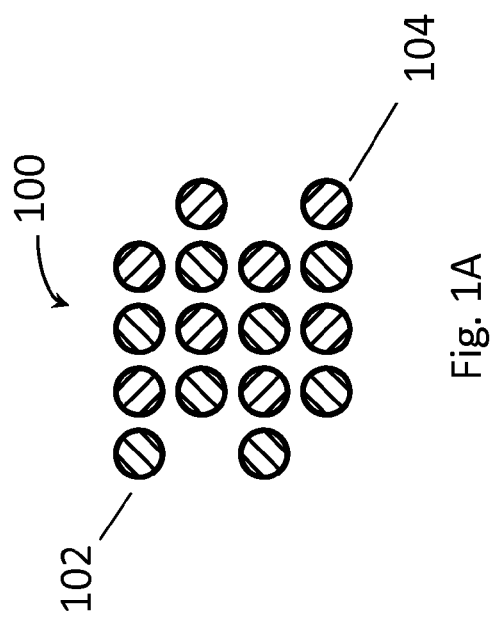
FIG. 1A shows a pattern of pressure detecting dots according to one embodiment.

The pattern of dots may be any desired pattern. FIG. 1A shows a pattern 100 of pressure detecting dots according to one embodiment. In the example of FIG. 1A, dots are arranged in a rectilinear pattern, with a dot of the pressure sensitive component 102 surrounded by four dots of the pressure reference component 104, and a dot of the pressure reference component 104 surrounded by four dots of the pressure sensitive component 102, except at the edges of the pattern. FIG. 1B shows a pattern 120 of pressure detecting dots according to another embodiment. In the example of FIG. 1B, the dots may be similarly interleaved using a hexagonal pattern, so that a dot of the pressure sensitive component 102 is surrounded by six dots of the pressure reference component 104, and a dot of the pressure reference component 104 is surrounded by six dots of the pressure sensitive component 102.

In other examples, a first region of the substrate may be populated with dots of the pressure sensitive component while a second region, for example adjacent to the first region, is populated with dots of the pressure reference component. The first region may be adjacent to, overlapping with, or spaced apart from the second region. FIG. 2A is a schematic view of a substrate 200 having a first region 202 populated with dots of the pressure sensitive component 102, and a second region 204, overlapping the first region 202, populated with dots of the pressure reference component 104. FIG. 2B is a schematic view of a substrate 220 having a first region 222 populated with dots of the pressure sensitive component 102, and a second region 224, adjacent to the first region 222, populated with dots of the pressure reference component 104.

In another aspect, a method of applying an environment sensitive coating to a substrate may be performed by positioning the substrate on a work surface of a fluid patterning apparatus, flowing an environment sensitive coating material to a dispenser of the fluid patterning apparatus, applying energy to the environment sensitive coating materials, and dispensing the environment sensitive coating material onto the substrate in a plurality of dots having a predetermined pattern. The environment sensing material may have one or more components, such as a pressure sensitive component and a pressure reference component.

The fluid patterning apparatus may be a 3D printer or an inkjet printer, as described above. The pressure sensitive component may be a composition compatible with 3D printing or inkjet printing that includes a light emitting material with a temperature and pressure dependent emission intensity, wherein the light emitting material is embedded, dispersed, or dissolved in an oxygen permeable matrix precursor that is compatible with 3D printing or inkjet printing. The pressure reference component may be a composition compatible with 3D printing or inkjet printing that includes the light emitting material embedded, dispersed, or dissolved in an oxygen impermeable matrix precursor that is compatible with 3D printing or inkjet printing.

The matrix precursors described above may be mixtures of polymerizable monomers that may be polymerized by application of energy, including radiant or mechanical heat energy, or UV energy. The monomer mixture may include a pre-polymerized portion, such as a masterbatch, to provide a target viscosity or viscosity profile suited to the fluid patterning apparatus being used. The polymerizable monomers may include any of the monomers described above, and either matrix precursor may have one monomer or more than one monomer.

The pressure sensitive component may be a light emitting material, complex, or mixture, such as a platinum porphyrin compound, for example tetra(pentafluorophenyl) porphine, embedded in an oxygen permeable matrix, such as a polymer. The copolymer of heptafluoro-n-butyl methacrylate and hexafluoroisopropyl methacrylate mentioned above may be used. The pressure reference component may be the same light emitting material, complex, or mixture embedded in an oxygen impermeable matrix, such as a polymer. The oxygen impermeable polymers enumerated above may be used.

In one aspect, the light emitting material, or luminophor, may be embedded in the respective matrices by applying mechanical energy to mix or disperse the light emitting material in the matrix. The polymers may be extruded or processed in a mixer, such as a Brabender mixer, to accomplish dispersion of the light emitting material. The softened materials may be fed under pressure to a dispenser of the 3D printer through piping or tubing that has heat input and/or heat conservation features, such as insulation and/or jacketing, to maintain flowability of the materials. The pressure sensitive component is flowed to the dispenser through a first pathway and the pressure reference component is flowed to the dispenser through a second pathway. A solvent may be included with the pressure sensitive component to control viscosity for flowing through the first pathway.

The dispenser is moved relative to the substrate to dispense a plurality of dots of each component on the substrate in a desired pattern. The patterns described above may be used. The pressure sensitive component is applied to the substrate in a first plurality of dots according to a first pattern executed by the 3D printer. The pressure reference component is also applied to the substrate in a second plurality of dots according to a second pattern executed by the 3D printer. In some cases, the first pattern and the second pattern interleave such that dots of pressure sensitive component may be located between dots of pressure reference component.

In another aspect, the pattern of dots may be made using an inkjet printer. The pressure sensitive and pressure reference components may be used directly in the dispensers of the inkjet printer by heating each component to an extent that a useable viscosity results. Alternately, a pressure sensitive precursor and a pressure reference precursor may be dispensed using the inkjet printer, and the patterned fluid hardened by curing or drying.

In one method, the pressure sensitive precursor is the pressure sensitive component dissolved in a solvent, and the pressure reference precursor is the pressure reference component dissolved in a solvent. Each precursor is dispensed onto the substrate, and then allowed to harden by drying. Energy may be applied at any stage of the process, for example as the precursors flow through the fluid patterning apparatus or after the precursors are patterned onto the substrate, to help in dissolving any of the precursors in the solvent, help flow the precursors through the fluid patterning apparatus, and/or help remove the solvent.

In another method, each of the pressure sensitive precursor and the pressure reference precursor includes the light emitting material and one or more monomers. Polymerization initiators and/or catalysts, such as peroxides, and solvents may be included. Additionally, pre-polymerized components, such as masterbatch pre-polymers, may also be included. The blend of each precursor may be adjusted to a target viscosity or viscosity profile to aid in dispensing through the fluid patterning apparatus.

Energy may be applied to each precursor in the embodiment above at any stage of the process to adjust viscosity or viscosity profile, to activate polymerization, to encourage dissolving in the solvent, or to drive away solvent, unreacted monomers, or oligomers. The energy may be radiant, conductive, or mechanical heat energy, or UV or visible radiation, and may be applied to one or more of the precursors as the precursor flows through the fluid patterning apparatus, or after the precursor is patterned onto the substrate. It should be noted that in some embodiments, one precursor may be applied to the substrate using a non-reactive application method, as described above, and another precursor may be applied to the substrate using a reactive application method. Additionally, one precursor may be applied to the substrate using 3D printing while another substrate is applied using inkjet printing. Finally, it should be noted that one component of the environment sensitive coating may be applied directly to the object being prepared for pressure analysis, while another component is applied to a portable substrate for adhesion to the object.

Oxygen permeability of the matrix for each of the pressure sensitive component and the pressure reference component may be adjusted based on the thickness of the matrix material, concentration of the light emitting material, and oxygen sensitivity of the light emitting material. If a highly sensitive compound is used in the pressure sensitive component, a less-permeable matrix may be useful in some embodiments to modulate the pressure response of the pressure sensitive component. A fraction of a less-permeable material may be mixed with the oxygen permeable material, for example by including monomers in the polymerization mixture that lead to less oxygen permeability. To first-order approximation, oxygen permeability of the resulting polymer follows molar fraction and permeability of the monomers. Thus, if monomer A has oxygen permeability of X and monomer B has oxygen permeability of Y, a mixture of 10 mole % A and 90 mole % B will have oxygen permeability of approximately 0.1X+0.9Y. If a highly sensitive light emitting material is used, the pressure reference component is normally made using a matrix of very low permeability, such as the poly(vinylidene chloride) matrix. However, if a less sensitive light emitting material is used, some slight permeability may be tolerated.

The environment sensitive coating may include a foundation coating in some embodiments. The foundation may include a layer of white material, such as a metal oxide white paint. The foundation coating may be applied between the substrate and the layer having the light emitting material, and may be used with the pressure sensitive component, the pressure reference component, or both. In some embodiments, an adhesion layer may also be used as part of the foundation layer. The adhesion layer may be a polymer compatible with the polymers being used as host materials for the light emitting material, and the material of the adhesion layer may be a UV stable material.

In one aspect, a method of sensing pressure or oxygen concentration in an oxygen-containing fluid adjacent to a substrate includes coating a substrate with an environment sensitive coating comprising a first portion with an oxygen sensitive light emitting material embedded in an oxygen permeable matrix and a second portion with the oxygen sensitive light emitting material embedded in an oxygen impermeable matrix; flowing an oxygen-containing fluid, which may be an oxygen-containing gas, over the environment sensitive coating; irradiating the oxygen sensitive light emitting material with light having a wavelength that stimulates the oxygen sensitive light emitting material to emit light; and measuring the intensity of light emitted by the oxygen sensitive light emitting material in the first portion and the second portion. The oxygen sensitive light emitting material is a material that has a luminous emission when irradiated by a stimulating radiation, such as ultraviolet radiation, and the luminous emission has an intensity that depends on partial pressure of oxygen in the fluid. The oxygen sensitive light emitting material may be a compound selected from the group consisting of tetra(pentafluorophenyl)porphine, platinum tetra(pentafluorophenyl)porpholactone, platinum tetrabenztetraphenyl porphine, platinum tetrabenzporphine, platinum tetra(heptafluoropropyl)porphine, and platinum octaethylporphyrin.

The oxygen permeable matrix may be any of the oxygen permeable polymers listed above, and the oxygen impermeable matrix may be any of the oxygen impermeable polymers listed above. The substrate may be coated with the first and second portion of the environment sensitive coating in a pattern selected to sense the pressure of the oxygen-containing fluid at desired locations along the surface of the substrate. For example, the first and second portions may be formed into a plurality of dots in the patterns described above. In other embodiments, continuous films of the first and second portions may be applied in alternating stripes on the surface of the substrate.

A single illumination source may be used in embodiments featuring a single light emitting material used for the pressure sensitive component and the pressure reference component. Likewise, a single detector may be used to detect the intensity of luminous emissions from the light emitting material. The illumination source illuminates the pressure sensitive and the pressure reference components such that all instances of the light emitting material absorb the illumination radiation. All instances likewise emit light at an indicative wavelength, each instance of the light emitting material emitting at an intensity that depends on temperature and pressure, for the pressure sensitive component, and on temperature alone for the pressure reference component. Measuring the intensity of the emission at each instance of light emitting material may include forming an image of all concurrent emissions.

The measured intensities of emitted light are converted into pressure or concentration values by relating the measured intensities to oxygen partial pressure. A ratio of the emission intensity of the pressure sensitive component to the emission intensity of the pressure reference component is formed at each instance of light emitting material so that a map of pressure along the surface of the substrate may be constructed. The emission image may be matched to the known pattern of the pressure sensitive component and the pressure reference component to map emission intensities to type of instance. The known dimensions of the pattern may then be used to interpolate between pressure sensitive instances and pressure reference instances, so that a ratio of the pressure sensitive and pressure reference intensities may be defined at each instance of light emitting material.

The ratio of pressure sensitive intensity to pressure reference intensity is commonly used to separate temperature dependence from pressure dependence so that oxygen sensitive light emitting materials may be used to indicate pressure. In this disclosure, the same light emitting material may be used to indicate both pressure/temperature dependence and temperature dependence only, thus removing sources of error arising from illuminating and detecting multiple wavelengths of light. Additionally, applying the pattern using 3D printing or inkjet printing improves the precision of application of the material to the substrate, reducing thickness and composition variation.

Figure 3:
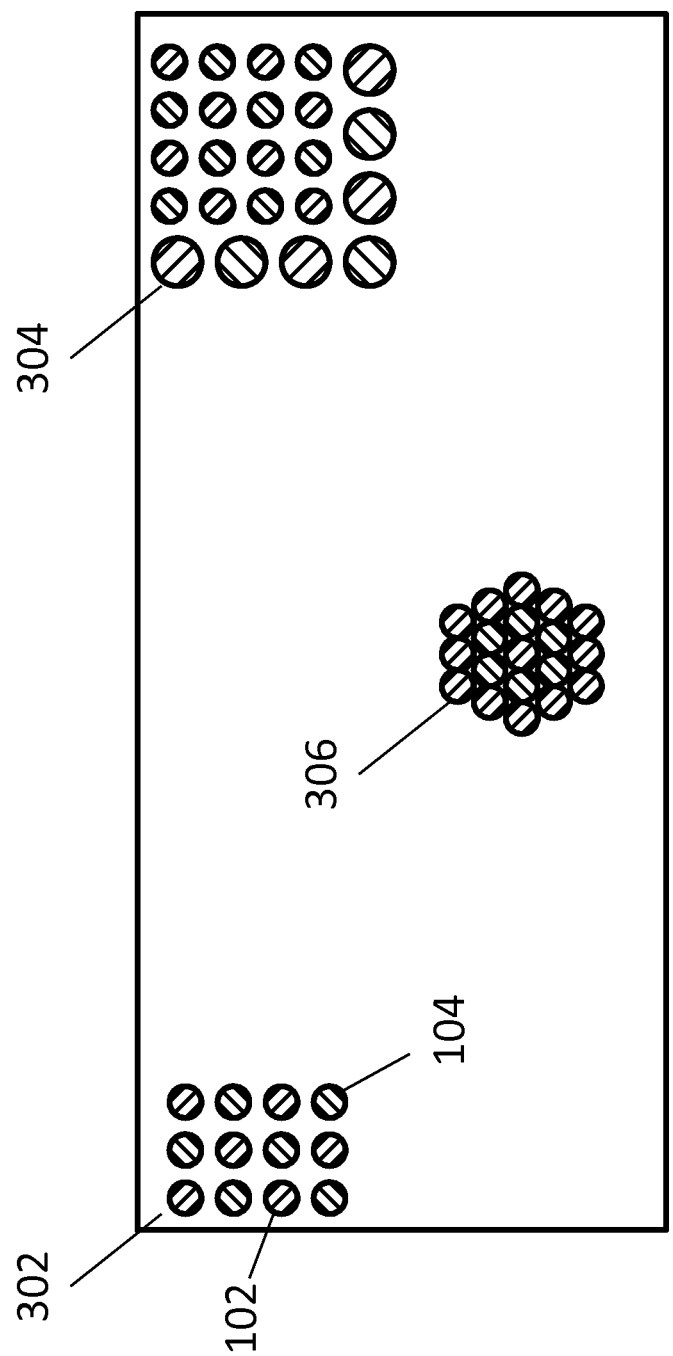
FIG. 3 is a schematic view of a substrate having pressure sensitive dots and pressure reference dots in three areas of the substrate separated by areas of the substrate not populated by dots, according to another embodiment.

The pattern may be a pattern of dots applied to locations of the substrate to be analyzed, with regions between the location to be analyzed having no dots. Additionally, density of the dots may be adjusted for coarser or finer resolution. FIG. 3 is a schematic view of a substrate 300 having pressure sensitive dots 102 and pressure reference dots 104 in three areas of the substrate 302, 304, and 306, separated by areas of the substrate not populated by dots. Each of the three areas 302, 304, and 306 has a different shape, density, and pattern of dots. The areas may be located at points on the substrate 300 where a pressure map along the surface of the substrate may be of particular interest. In some cases, the substrate 300 may be an aerodynamic object, such as an aircraft, spacecraft, aircraft or spacecraft part model, or other object on which pressure analysis is to be performed.

In another aspect, an environment sensitive coating, as described above, may be applied to a portable foundation substrate, which may then be applied to an object for pressure analysis. For example, the environment sensitive coating may be applied to a polymer film that is subsequently adhered to the object. A pattern of dots may be mapped from locations of interest on the object to a flat surface using conformal mapping software. The pattern of dots may be dispensed onto the flat polymer film, and then the film may be adhered to the object.

As noted above, the pattern of dots formed on the substrate may include dots of any convenient size. Dots available using 3D printers may have a dimension as small as 0.1 mm. Smaller dots, for example dots as small as 0.01 mm, are available using inkjet printers. The dots may also have thickness less than 0.1 mm, such as less than 50 µm, for example less than 30 µm. Thickness and dimensional uniformity available with some 3D printers may exceed 99.5%, meaning that deviation of thickness or dimension from an average value is less than about 0.5% of the average value.

While the foregoing is directed to various embodiments, other and further embodiments may be devised without departing from the basic scope of the methods, compositions, and apparatus described herein, and the scope of what is claimed below is not limited to the disclosed embodiments.

What is claimed is:

1. A method of applying an environment sensitive coating system to a substrate, comprising:
    applying a pressure sensitive component comprising a first portion of an oxygen sensitive light emitting material embedded in an oxygen permeable binder in a first pattern to the substrate; and
    applying a pressure reference component comprising a second portion of the oxygen sensitive light emitting material embedded in an oxygen impermeable binder in a second pattern to the substrate, wherein at least one of the first and the second patterns comprises a plurality of discrete dots having a lateral dimension less than 0.1 mm and a thickness less than 0.1 mm.

2. The method of claim 1, wherein applying the pressure sensitive component in the first pattern comprises depositing a flowable pressure sensitive precursor comprising the first portion of the oxygen sensitive light emitting material and the oxygen permeable binder to the substrate according to the first pattern and hardening the flowable pressure sensitive precursor to form the pressure sensitive component; and wherein applying the pressure reference component in the second pattern comprises depositing a flowable pressure reference precursor comprising the second portion of the oxygen sensitive light emitting material and the oxygen impermeable binder to the substrate according to the second pattern and hardening the flowable pressure reference precursor to form the pressure reference component.

3. The method of claim 1, wherein the oxygen permeable binder and the oxygen impermeable binder are each usable for 3D printing or inkjet printing.

4. A method of applying an environment sensitive coating system to a substrate, comprising:
    applying a pressure sensitive component comprising a first portion of an oxygen sensitive light emitting material embedded in an oxygen permeable binder in a first pattern to the substrate; and
    applying a pressure reference component comprising a second portion of the oxygen sensitive light emitting material embedded in an oxygen impermeable binder in a second pattern to the substrate, wherein applying the pressure sensitive component in the first pattern comprises depositing a flowable pressure sensitive precursor comprising the first portion of the oxygen sensitive light emitting material and the oxygen permeable binder to the substrate according to the first pattern and hardening the flowable pressure sensitive precursor to form the pressure sensitive component; and wherein applying the pressure reference component in the second pattern comprises depositing a flowable pressure reference precursor comprising the second portion of the oxygen sensitive light emitting material and the oxygen impermeable binder to the substrate according to the second pattern and hardening the flowable pressure reference precursor to form the pressure reference component, and wherein depositing the flowable pressure sensitive precursor and the flowable pressure reference precursor to the substrate is performed using a 3D printer.

5. A method of applying an environment sensitive coating system to a substrate, comprising:
    applying a pressure sensitive component comprising a first portion of an oxygen sensitive light emitting material embedded in an oxygen permeable binder in a first pattern to the substrate; and applying a pressure reference component comprising a second portion of the oxygen sensitive light emitting material embedded in an oxygen impermeable binder in a second pattern to the substrate, wherein applying the pressure sensitive component in the first pattern comprises depositing a flowable pressure sensitive precursor comprising the first portion of the oxygen sensitive light emitting material and the oxygen permeable binder to the substrate according to the first pattern and hardening the flowable pressure sensitive precursor to form the pressure sensitive component; and wherein applying the pressure reference component in the second pattern comprises depositing a flowable pressure reference precursor comprising the second portion of the oxygen sensitive light emitting material and the oxygen impermeable binder to the substrate according to the second pattern and hardening the flowable pressure reference precursor to form the pressure reference component, and wherein depositing the flowable pressure sensitive precursor to the substrate comprises:

positioning the substrate on a work surface of a 3D printer;

flowing the flowable pressure sensitive precursor to a dispenser of the 3D printer;

applying energy to the flowable pressure sensitive precursor; and dispensing the flowable pressure sensitive precursor onto the substrate in a plurality of dots according to the first pattern; and wherein hardening the flowable pressure sensitive precursor comprises curing the flowable pressure sensitive precursor.

6. The method of claim 5, wherein depositing the flowable pressure reference precursor to the substrate comprises:

positioning the substrate on a work surface of a 3D printer;

flowing the flowable pressure reference precursor to a dispenser of the 3D printer;

applying energy to the flowable pressure reference precursor; and dispensing the flowable pressure reference precursor onto the substrate in a plurality of dots according to the second pattern; and wherein hardening the flowable pressure reference precursor comprises curing the flowable pressure reference precursor.

7. A method of applying an environment sensitive coating system to a substrate, comprising:

applying a pressure sensitive component comprising a first portion of an oxygen sensitive light emitting material embedded in an oxygen permeable binder in a first pattern to the substrate; and applying a pressure reference component comprising a second portion of the oxygen sensitive light emitting material embedded in an oxygen impermeable binder in a second pattern to the substrate, wherein applying the pressure sensitive component in the first pattern comprises depositing a flowable pressure sensitive precursor comprising the first portion of the oxygen sensitive light emitting material and the oxygen permeable binder to the substrate according to the first pattern and hardening the flowable pressure sensitive precursor to form the pressure sensitive component; and wherein applying the pressure reference component in the second pattern comprises depositing a flowable pressure reference precursor comprising the second portion of the oxygen sensitive light emitting material and the oxygen impermeable binder to the substrate according to the second pattern and hardening the flowable pressure reference precursor to form the pressure reference component, and wherein depositing the flowable pressure sensitive precursor to the substrate comprises:

positioning the substrate on a work surface of an inkjet printer;

flowing the flowable pressure sensitive precursor to one or more dispensers of the inkjet printer; and dispensing the flowable pressure sensitive precursor onto the substrate in a plurality of dots according to the first pattern; and wherein hardening the flowable pressure sensitive precursor comprises curing the flowable pressure sensitive precursor.

8. The method of claim 7, wherein depositing the flowable pressure reference precursor to the substrate comprises:

positioning the substrate on a work surface of an inkjet printer;

flowing the flowable pressure reference precursor to one or more dispensers of the inkjet printer; and dispensing the flowable pressure reference precursor onto the substrate in a plurality of dots according to the second pattern; and wherein hardening the flowable pressure reference precursor comprises curing the flowable pressure reference precursor.

9. A method of applying an environment sensitive coating system to a substrate, comprising:

applying a pressure sensitive component comprising a first portion of an oxygen sensitive light emitting material embedded in an oxygen permeable binder in a first pattern to the substrate; and applying a pressure reference component comprising a second portion of the oxygen sensitive light emitting material embedded in an oxygen impermeable binder in a second pattern to the substrate, wherein applying the pressure sensitive component in the first pattern comprises depositing a flowable pressure sensitive precursor comprising the first portion of the oxygen sensitive light emitting material and the oxygen permeable binder to the substrate according to the first pattern and hardening the flowable pressure sensitive precursor to form the pressure sensitive component; and wherein applying the pressure reference component in the second pattern comprises depositing a flowable pressure reference precursor comprising the second portion of the oxygen sensitive light emitting material and the oxygen impermeable binder to the substrate according to the second pattern and hardening the flowable pressure reference precursor to form the pressure reference component, and wherein depositing the flowable pressure sensitive precursor and depositing the flowable pressure reference precursor are both performed using an inkjet printer.

10. A method of applying an environment sensitive coating to a substrate comprising:

positioning the substrate on a work surface of a fluid patterning apparatus;

flowing a first environment sensitive coating precursor comprising a first portion of an oxygen sensitive light emitting material embedded in an oxygen permeable binder to a dispenser of the fluid patterning apparatus;

applying energy to the first environment sensitive coating precursor;

dispensing the first environment sensitive coating precursor onto the substrate in a first plurality of dots having a first predetermined pattern;

flowing a second environment sensitive coating precursor comprising a second portion of the oxygen sensitive light emitting material embedded in an oxygen impermeable binder to the dispenser of the fluid patterning apparatus;

dispensing the second environment sensitive coating precursor onto the substrate in a second plurality of dots having a second predetermined pattern; and curing the first and second environment sensitive coating precursors to form the environment sensitive coating, wherein each of the dots in the first and second plurality of dots has a lateral dimension less than 0.1 mm and a thickness less than 0.1 mm.

11. The method of claim 10, wherein each of the first and second environment sensitive coating precursors comprises one or more polymerizable monomers and a light emitting material.

12. The method of claim 11, wherein the environment sensitive coating comprises a pressure sensitive component and a pressure reference component.

13. The method of claim 12, wherein the pressure sensitive component comprises the oxygen permeable polymer and the oxygen sensitive light emitting material.

14. The method of claim 12, wherein the pressure reference component comprises the oxygen impermeable polymer and the oxygen sensitive light emitting material.

15. The method of claim 12, wherein the first and second environment sensitive coating precursors are provided to the dispenser through separate pathways.

16. The method of claim 15, wherein the first and second patterns form an interleaved pattern of dots.

17. The method of claim 16, wherein the interleaved pattern comprises a varying density of dots.

18. The method of claim 17, wherein the fluid patterning apparatus is a 3D printer or an inkjet printer.

* * * * *